(12) United States Patent
Jensen et al.

(10) Patent No.: US 6,589,514 B2
(45) Date of Patent: Jul. 8, 2003

(54) **COSMETIC INTENSIVE REPAIR SERUM WITH *MORINDA CITRIFOLIA***

(75) Inventors: Claude Jarkae Jensen, Cedar Hills, UT (US); Heidi Robinson, Orem, UT (US)

(73) Assignee: Morinda, Inc., Provo, UT (US)

( * ) Notice: Subject to any disclaimer, the term of this patent is extended or adjusted under 35 U.S.C. 154(b) by 0 days.

(21) Appl. No.: 09/836,869

(22) Filed: Apr. 17, 2001

(65) Prior Publication Data

US 2002/0192246 A1 Dec. 19, 2002

(51) Int. Cl.⁷ .............................. A61K 7/42; A61K 7/44; A61K 7/48; A61K 31/70; A61K 31/355
(52) U.S. Cl. ...................... 424/59; 424/60; 424/195.15; 424/195.17; 424/401; 424/725; 424/729; 424/740; 424/744; 424/752; 424/764; 424/766; 424/777; 514/23; 514/458; 514/474; 514/725; 514/783; 514/844
(58) Field of Search .................................. 424/400, 401, 424/59, 60, 195.17, 195.15, 725, 764, 777, 752, 744, 729, 740, 766; 514/23, 783, 844, 458, 474, 725

(56) References Cited

U.S. PATENT DOCUMENTS 5,288,491 A * 2/1994 Moniz ........................ 424/769
6,214,351 B1 * 4/2001 Wadsworth et al. ........ 424/769

FOREIGN PATENT DOCUMENTS

JP   02000095663 A  *  4/2000

OTHER PUBLICATIONS

Botanical Benefits Irish Moss Hand & Body Lotion (http://www.a-better-way.com/catalog/personal.html ©2001).*
"Rachel Perry Environmental Skin Protector SPF 18", Product Alert, V. 29, No. 2, Jan. 25, 1999.*

* cited by examiner

Primary Examiner—Jose' G. Dees
Assistant Examiner—Marina Lamm
(74) Attorney, Agent, or Firm—Kirton & McConkie; Michael F. Krieger

(57) ABSTRACT

The present invention advances prior art intensive repair serums by providing an intensive repair serum formulated with *Morinda citrifolia* from the Indian Mulberry plant. The addition of *Morinda citrifolia* to the serum of the present invention serves to provide significant skin care advantages not found in prior art intensive repair serums.

59 Claims, No Drawings

COSMETIC INTENSIVE REPAIR SERUM WITH *MORINDA CITRIFOLIA*

BACKGROUND

1. Field of the Invention

The present invention relates generally to a protective formula for the skin and, more particularly, to a composition optimized for treating and repairing the skin especially in application to damaged skin in the form of a serum or rejuvenating ointment or cream.

2. Background

The skin is made up of several layers, or two major layers. The stratum corneum, or epidermis, is the top layer and forms a protective covering for the skin and controls the flow of water and substances in and out of the skin. This is known as a barrier function. To stay healthy, the skin has to cope with changing environmental conditions and repair damages at the same time. The skin is in a constant state of repair as it sheds the dead cells on the surface and replenishes the lower layers. The lower level of the skin is known as the dermis. The dermis is the layer which provides the strength, elasticity and the thickness to the skin.

The main cell type of the dermis is fibroblasts, which is responsible for synthesis and secretion of all the dermal matrix components such as collagen, elastin and glycosaminoglycans. Collagen provides the strength, elastin the elasticity, and glycosaminoglycans the moistness and plumpness of the skin.

The skin is often abused by soaps, emulsifier-based cosmetics, hot water, or organic solvents. These each contribute to rob the skin of essential moisture, and to create a stressed barrier that does not function properly. Moisture loss and irritation increases, leaving the skin sensitive, scaly, and dry. Free-radical activity multiplies, causing more wrinkles and premature aging.

Furthermore, the skin is subject to deterioration through dermatological disorders, environmental abuse (wind, air conditioning, central heating) or through the normal aging process (chronoaging), which may be accelerated by exposure of skin to sun (photoaging). The thickness of the dermal layer is reduced due to aging, thus causing the skin to slacken. This is believed to be partially responsible for the formation of wrinkles. In recent years the demand for cosmetic compositions and cosmetic methods for improving the appearance and condition of skin has grown enormously.

Consumers are increasingly seeking "anti-aging" cosmetic products which treat or delay the visible signs of actual aging and weathered skin such as wrinkles, lines, sagging, hyperpigmentation and age spots. Consumers also frequently seek other benefits from cosmetic products in addition to anti-aging. The concept of "sensitive skin" has raised the demand for cosmetic products which improve the appearance and condition of sensitive, dry and/or flaky skin and to soothe red, and/or irritated skin. Consumers also desire cosmetic products that treat spots, pimples, blemishes etc.

Research shows that using a skin care product that includes the skin's natural building blocks speeds the skin's ability to repair itself and keeps the barrier function at optimal levels. This approach treats the problem, not the symptom. Irritation stops before it can start so recurring problems are avoided, thus bringing the skin back to ideal conditions.

The consumer demand for "natural" based products has been growing in recent years. Chemical synthesis is perceived as environmentally unsafe. A chemically synthesized ingredient may contain harsh chemicals. Natural products are perceived as pure and mild and superior to chemically synthesized products. Delivering a cosmetic benefit from plant sources, however, is not trivial. In order to derive a real benefit from a "natural" source, not only does a plant or a part of the plant containing a specific active have to be identified, but a minimum concentration and/or a specific extract of that plant has to be identified which truly delivers a cosmetic benefit.

Accordingly, consumers demand an effective treatment for the skin and wrinkles that moisturizes, heals, and soothes the vulnerable and delicate surface of the skin. Further, consumers demand that treatment for the skin be based on "natural" products to promote healing and preserve youthful appearance.

SUMMARY OF THE INVENTION

The firmer the skin is, the more youthful its appearance will be. While firm and tone skin is optimal, many factors exist that invariably cause the skin to slacken and lose its youthful look over time. The slackening of the skin is the first and most visible sign of aging and the main cause of wrinkles and lines. In addition, premature aging can be accelerated by exposure to UV rays, pollution, heat, and over-dieting.

The importance of using an anti-aging intensive repair serum in a daily skin care regime, as well as the advantages and benefits that stem from the introduction of *Morinda citrifolia* to the body, are recognized herein. As such, the present invention advances prior art serums by providing an anti-aging serum formulated with *Morinda citrifolia*, as manufactured and produced by Morinda, Inc. of Orem, Utah under the trademark TAHITIAN NONI, from the Indian Mulberry plant. The addition of *Morinda citrifolia* to the anti-aging repair serum of the present invention serves to provide significant skin care advantages not found in prior art anti-aging repair serums.

Therefore, it is an object of the preferred embodiments of the present invention to provide an anti-aging and repair serum formulated with *Morinda citrifolia*.

It is another object of the preferred embodiments of the present invention to provide an anti-aging and repair serum formulated with *Morinda citrifolia* that nourishes the health of the skin.

It is another object of the preferred embodiments of the present invention to provide an anti-aging and repair serum formulated with *Morinda citrifolia* that responds to the loss of skin tone and helps diminish the appearance of fine lines and visible signs of aging.

It is still another object of the preferred embodiments of the present invention to provide an anti-aging and repair serum formulated with *Morinda citrifolia* that promotes immediate and continuous benefits to effectively boost hydration and firmness of the surface layer of the skin to maintain soft, supple, lustrous skin.

It is a further object of the preferred embodiments of the present invention to provide an anti-aging and repair serum formulated with *Morinda citrifolia* that stimulates the body's natural production of collagen.

It is still a further object of the preferred embodiments of the present invention to provide an anti-aging and repair serum formulated with *Morinda citrifolia* that restores visible tone and elasticity to the surface of the skin.

It is still a further object of the preferred embodiments of the present invention to provide an anti-aging and repair serum formulated with *Morinda citrifolia* that minimizes the apparent effects of environmental agitators such as pollution, sun, and stress.

It is yet another object of the preferred embodiments of the present invention to provide an anti-aging and repair serum formulated with *Morinda citrifolia* that works to repair the underlying layers of the skin and to help the skin retain youthful radiance with the use of antioxidants and other beneficial ingredients.

The *Morinda citrifolia* enhanced anti-aging and repair serum of the present invention provides all of the beneficial functions of prior art anti-aging and repair serums such as revitalizing and smoothing the skin, restoring moisture to the skin, and providing firmer, more youthful looking skin. In addition to these beneficial functions, the *Morinda citrifolia* enhanced anti-aging and repair serum of the present invention helps to minimize the visible signs of both biological and environmental aging, while at the same time, meeting the specific needs of the skin. *Morinda citrifolia* is high in antioxidants that help to fight free-radical damage caused by the sun and other elements. *Morinda citrifolia* is also rich in linoleic acid, which is an essential fatty acid with specific abilities for nourishing the health of the skin. Each of these, along with the other ingredients, aids in barrier repair and protection, or repair and protection of the stratum corneum.

To achieve the foregoing objects, and in accordance with the invention as embodied and broadly described herein, the present invention features an anti-aging and repair serum comprising several key ingredients. These ingredients comprise *Morinda citrifolia*, hydrolyzed algin and *chlorella vulgaris* extract (type 1-4), *rosmarinus officinalis* extract and lecithin, Sodium PCA, and *hypnea musciformis* extract and mugwort (*artemisia vulgaris*). A portion of, or all of these ingredients may be combined with other ingredients commonly found in anti-aging and repair serum formulations.

In addition to these key ingredients, the anti-aging and repair serum of the present invention also comprises essential oils and a suitable carrier composition.

DETAILED DESCRIPTION OF SPECIFIC EMBODIMENTS

It will be readily understood that the components of the present invention, as generally described herein, could be arranged and designed in a wide variety of different formulations. Thus, the following more detailed description of the embodiments of the compositions or formulations of the present invention are not intended to limit the scope of the invention, as claimed, but are merely representative of the presently preferred embodiments of the invention.

The present invention includes topical compositions that contain a vegetable composition derived from *Morinda citrifolia* as an ingredient in a suitable carrier for application to the skin for intensive repair.

The stratum corneum is the layer of the skin that forms the top surface layer and serves to protect the skin while controlling moisture and the flow of substances in and out of the skin. As this barrier function is broken down, the skin suffers damaging effects, thus creating or contributing to premature aging. These damaging effects causing premature aging of the skin are a concern for many individuals wishing to maintain healthy, youthful looking and feeling skin. To stay healthy, the skin must be able to cope with the changing environmental conditions and damaging elements it is exposed to, while also repairing itself at the same time. The skin is in a constant state of repair as it sheds the dead cells on the surface and replenishes the lower layers.

The skin is often abused by soaps, emulsifier-based cosmetics, hot water, or organic solvents. These each contribute to rob the skin of essential moisture, and to create a stressed barrier that does not function properly. Moisture loss and irritation increases, leaving the skin sensitive, scaly, and dry. Free-radical activity multiplies, causing more wrinkles and premature aging.

Furthermore, the skin is subject to deterioration through dermatological disorders, environmental abuse (wind, air conditioning, central heating) or through the normal aging process (chronoaging), which may be accelerated by exposure of skin to sun (photoaging). The thickness of the dermal layer is reduced due to aging, thus causing the skin to slacken. This is believed to be partially responsible for the formation of wrinkles. In recent years the demand for cosmetic compositions and cosmetic methods for improving the appearance and condition of skin has grown enormously.

The present invention discloses an "anti-aging" cosmetic product which treats the skin and delays the visible signs of actual aging and weathered skin such as wrinkles, lines, sagging, hyperpigmentation and age spots. The present invention also decreases the appearance and condition of sensitive, dry and/or flaky skin, serves to soothe red, and/or irritated skin, and treats spots, pimples, blemishes, and other skin irregularities.

The present invention employs an intensive repair serum formulated with the skin's natural building blocks that speeds the skin's ability to repair itself and keeps the barrier function at optimal levels. This approach treats the problem, not the symptom. Irritation stops before it can start so recurring problems are avoided, thus bringing the skin back to ideal conditions.

The demand for "natural" based products has grown in recent years, due to the perception that chemical synthesis is environmentally unsafe. A chemically synthesized ingredient may contain harsh chemicals. However, natural products are perceived as pure and mild and superior to chemically synthesized products. Delivering a cosmetic benefit from plant sources, however, is not trivial. In order to derive a real benefit from a "natural" source, not only does a plant or a part of the plant containing a specific active have to be identified, but a minimum concentration and/or a specific extract of that plant has to be identified which truly delivers a cosmetic benefit.

As such, the present invention discloses an intensive repair serum that is formulated with *Morinda citrifolia* extract and other key ingredients to provide a natural and effective skin repair serum. The advantages and benefits of *Morinda citrifolia* are discussed below along with a description of the key ingredients of the present invention.

I. General Discussion of *Morinda Citrifolia*

The Indian Mulberry plant, known scientifically as *Morinda Citrifolia L.*, is a shrub or small tree up to 10 m in height. The leaves are oppositely arranged with an elliptic to ovate form. The small white flowers are contained in a fleshy, globose, head-like cluster. The fruits are large, fleshy, and ovoid. At maturity, they are creamy-white and edible, but have an unpleasant taste and odor. The plant is native to Southeast Asia and has spread in early times to a vast area from India to eastern Polynesia. It grows randomly in the wild, and it has been cultivated in plantations and small individual growing plots. The *Morinda citrifolia* flowers develop into compound fruits composed of many small drupes fused into an ovoid, ellipsoid or roundish, lumpy body, with waxy, white, or greenish-white or yellowish, semi-translucent skin. The fruit contains "eyes" on its surface, similar to a potato. The fruit is juicy, bitter, dull-yellow or yellowish-white, and contains numerous red-brown, hard, oblong-triangular, winged 2-celled stones, each containing four seeds.

When fully ripe, the fruit has a pronounced odor like rancid cheese. Although the fruit has been eaten by several nationalities as food, the most common use of the *Morinda citrifolia* plant was as a red and yellow dye source. Recently, there has been an interest in the nutritional and health benefits of the *Morinda citrifolia* plant, further discussed below.

The present invention utilizes the fruit juice and the oil extracted from the *Morinda Citrifolia* plant. In a currently preferred process of producing *Morinda citrifolia* juice, the fruit is either hand picked or picked by mechanical equipment. The fruit can be harvested when it is at least one inch (2–3 cm) and up to 12 inches (24–36 cm) in diameter. The fruit preferably has a color ranging from a dark green through a yellow-green up to a white color, and gradations of color in between. The fruit is thoroughly cleaned after harvesting and before any processing occurs.

The fruit is allowed to ripen or age from 0 to 14 days, with most fruit being held from 2 to 3 days. The fruit is ripened or aged by being placed on equipment so it does not contact the ground. It is preferably covered with a cloth or netting material during aging, but can be aged without being covered. When ready for further processing the fruit is light in color, from a light green, light yellow, white or translucent color. The fruit is inspected for spoilage or for excessively green color and hard firmness. Spoiled and hard green fruit is separated from the acceptable fruit.

The ripened and aged fruit is preferably placed in plastic lined containers for further processing and transport. The containers of aged fruit can be held from 0 to 30 days. Most fruit containers are held for 7 to 14 days before processing. The containers can optionally be stored under refrigerated conditions prior to further processing. The fruit is unpacked from the storage containers and is processed through a manual or mechanical separator. The seeds and peel are separated from the juice and pulp.

The juice and pulp can be packaged into containers for storage and transport. Alternatively, the juice and pulp can be immediately processed into finished juice product. The containers can be stored in refrigerated, frozen, or room temperature conditions. The *Morinda citrifolia* juice and puree are preferably blended in a homogenous blend, after which they may be mixed with other ingredients, such as flavorings, sweeteners, nutritional ingredients, botanicals, and colorings. The finished juice product is preferably heated and pasteurized at a minimum temperature of 181 degrees F. (83 degrees C.) or higher up to 212 degrees F. (100 degrees C.).

The product is filled and sealed into a final container of plastic, glass, or another suitable material that can withstand the processing temperatures. The containers are maintained at the filling temperature or may be cooled rapidly and then placed in a shipping container. The shipping containers are preferably wrapped with a material and in a manner to maintain or control the temperature of the product in the final containers.

The juice and pulp are further processed by separating the pulp from the juice through filtering equipment. The filtering equipment preferably consists of, but is not limited to, a centrifuge decanter, a screen filter with a size from 1 micron up to 2000 microns, more preferably less than 500 microns, a filter press, reverse osmosis filtration., and any other standard commercial filtration devices. The operating filter pressure preferably ranges from 0.1 psig up to about 1000 psig. The flow rate preferably ranges from 0.1 g.p.m. up to 1000 g.p.m., and more preferably between 5 and 50 g.p.m. The wet pulp is washed and filtered at least once and up to 10 times to remove any juice from the pulp. The wet pulp typically has a fiber content of 10 to 40 percent by weight. The wet pulp is preferably pasteurized at a temperature of 181 degrees F. (83 degrees C.) minimum and then packed in drums for further processing or made into a high fiber product.

The method for extracting and processing the oil is described in co-pending application Ser. No. 09/384,785, filed on Aug. 27, 1999, which is incorporated by reference herein. *Morinda citrifolia* oil typically includes a mixture of several different fatty acids as triglycerides, such as palmitic, stearic, oleic, and linoleic fatty acids, and other fatty acids present in lesser quantities. In addition, the oil preferably includes an antioxidant to inhibit spoilage of the oil. Conventional food grade antioxidants are preferably used.

The *Morinda citrifolia* plant is rich in natural ingredients. Those ingredients that have been discovered include: from the leaves: alanine, anthraquinones, arginine, ascorbic acid, aspartic acid, calcium, beta-carotene, cysteine, cystine, glycine, glutamic acid, glycosides, histidine, iron, leucine, isoleucine, methionine, niacin, phenylalanine, phosphorus, proline, resins, riboflavin, serine, beta-sitosterol, thiamine, threonine, tryptophan, tyrosine, ursolic acid, and valine; from the flowers: acacetin-7-o-beta-d(+)-glucopyranoside, 5,7-dimethyl-apigenin-4'-o-beta-d(+)-galactopyranoside, and 6,8-dimethoxy-3-methylanthraquinone-1-o-beta-rhamnosyl-glucopy ranoside; from the fruit: acetic acid, asperuloside, butanoic acid, benzoic acid, benzyl alcohol, 1-butanol, caprylic acid, decanoic acid, (E)-6-dodeceno-gamma-lactone, (Z,Z,Z)-8,11,14-eicosatrienoic acid, elaidic acid, ethyl decanoate, ethyl hexanoate, ethyl octanoate, ethyl palmitate, (Z)-6-(ethylthiomethyl)benzene, eugenol, glucose, heptanoic acid, 2-heptanone, hexanal, hexanamide, hexanedioic acid, hexanoic acid (hexoic acid), 1-hexanol, 3-hydroxy-2-butanone, lauric acid, limonene, linoleic acid, 2-methylbutanoic acid, 3-methyl-2-buten-1-ol, 3-methyl-3-buten-1-ol, methyl decanoate, methyl elaidate, methyl hexanoate, methyl 3-methylthio-propanoate, methyl octanoate, methyl oleate, methyl palmitate, 2-methylpropanoic acid, 3-methylthiopropanoic acid, myristic acid, nonanoic acid, octanoic acid (octoic acid), oleic acid, palmitic acid, potassium, scopoletin, undecanoic acid, (Z,Z)-2,5-undecadien-1-ol, and vomifol; from the roots: anthraquinones, asperuloside (rubichloric acid), damnacanthal, glycosides, morindadiol, morindine, morindone, mucilaginous matter, nor-damnacanthal, rubiadin, rubiadin monomethyl ether, resins, soranjidiol, sterols, and trihydroxymethyl anthraquinone-monomethyl ether; from the root bark: alizarin, chlororubin, glycosides (pentose, hexose), morindadiol, morindanigrine, morindine, morindone, resinous matter, rubiadin monomethyl ether, and soranjidiol; from the wood: anthragallol-2,3-dimethylether; from the tissue culture: damnacanthal, lucidin, lucidin-3-primeveroside, and morindone-6beta-primeveroside; from the plant: alizarin, alizarin-alpha-methyl ether, anthraquinones, asperuloside, hexanoic acid, morindadiol, morindone, morindogenin, octanoic acid, and ursolic acid.

Recently, many health benefits have been discovered stemming from the use of products containing *Morinda citrifolia*. The benefit of *Morinda citrifolia* is found in its ability to isolate and produce Xeronine, a relatively small alkaloid physiologically active within the body. Xeronine occurs in practically all healthy cells of plants, animals and microorganisms. Even though *Morinda citrifolia* has a negligible amount of free xeronine, it contains appreciable amounts of the precursor of xeronine, called Proxeronine. Further, *Morinda citrifolia* contains the inactive form of the enzyme Proxeronase which releases Xeronine from proxeronine. A paper entitled, "The Pharmacologically Active Ingredient of Noni" by R. M. Heinicke of the University of Hawaii, indicates that *Morinda citrifolia* is "the best raw material to use for the isolation of xeronine," because of the building blocks of proxeronine and proxeronase. These building blocks aid in the isolation and production of Xeronine within the body. The function of the essential nutrient Xeronine is fourfold.

First, Xeronine serves to activate dormant enzymes found in the small intestines. These enzymes are critical to efficient digestion, calm nerves, and overall physical and emotional energy.

Second, Xeronine protects and keeps the shape and suppleness of protein molecules so that they may be able to pass through the cell walls and be used to form healthy tissue. Without these nutrients going into the cell, the cell cannot perform its job efficiently. Without pro-xeronine to produce xeronine our cells, and subsequently the body, suffer.

Third, Xeronine assists in enlarging the membrane pores of the cells. This enlargement allows for larger chains of peptides (amino acids or proteins) to be admitted into the cell. If these chains are not used they become waste.

Fourth, Xeronine, which is made from pro-xeronine, assists in enlarging the pores to allow better absorption of nutrients.

Each tissue has cells which contain proteins which have receptor sites for the absorption of xeronine. Certain of these proteins are the inert forms of enzymes which require absorbed Xeronine to become active. Thus Xeronine, by converting the body's procollagenase system into a specific protease, quickly and safely removes the dead tissue from skin. Other proteins become potential receptor sites for hormones after they react with Xeronine. Thus the action of *Morinda citrifolia* in making a person feel well is probably caused by Xeronine converting certain brain receptor proteins into active sites for the absorption of the endorphin, the well being hormones. Other proteins form pores through membranes in the intestines, the blood vessels and other body organs. Absorbing Xeronine on these proteins changes the shape of the pores and thus affects the passage of molecules through the membranes.

Because of its many benefits, *Morinda citrifolia* has been known to provide a number of anecdotal effects in individuals having cancer, arthritis, headaches, indigestion, malignancies, broken bones, high blood pressure, diabetes, pain, infection, asthma, toothache, blemishes, immune system failure, and others.

In addition to the numerous health benefits, *Morinda citrifolia* also provides significant benefits to the skin. *Morinda citrifolia* is high in antioxidants that help to fight free-radical damage caused by the sun and other changing environmental conditions and elements. To stay healthy, the skin must cope with these elements and conditions and repair the damage caused at the same time. The skin is in a constant state of repair as it sheds the dead cells on the surface and replenishes the lower layers.

*Morinda citrifolia* is also especially rich in linoleic acid, which is an essential fatty acid having the specific ability to nourish the health of the skin. As mentioned above, the skin is often abused by soaps, emulsifier-based cosmetics, hot water, organic solvents, etc., thus robbing essential moisture from the skin, and creating a stressed barrier that doesn't function properly. Moisture loss and irritation increases, leaving the skin sensitive, scaly, and dry. Free radical activity multiplies, causing more wrinkles and premature aging. *Morinda citrifolia* combats this problem by providing the essential fatty acids necessary to achieve and maintain healthy and youthful looking skin.

II. *Morinda citrifolia* Enhanced Anti-aging and Intensive Repair Serum

The present invention advances prior art intensive repair serums by providing an intensive repair serum formulated with *Morinda citrifolia* fruit juice from the Indian Mulberry plant. The *Morinda citrifolia* fruit juice is incorporated into various carriers suitable for application to the skin and is applied to damaged areas needing intensive repair. *Morinda Citrifolia* fruit juice extract is present in selected specific embodiments from about 0.1 to 80 percent by weight of the total weight of the composition. The carrier is present from about 20 to 80 percent by weight of the total composition. *Morinda citrifolia* oil extract may also be present in an amount from about 0.1–10 percent by weight. Additional elements such as colorants, fragrances, and other ingredients, such as skin protectants, may also be present.

The present invention also features a formulation comprising several key ingredients. These ingredients comprise *Morinda citrifolia*, hydrolyzed algin and *chlorella vulgaris* extract (type 1-4), rosmarinus officinalis extract and lecithin, Sodium PCA, and *hypnea musciformis* extract and mugwort (*artemisia vulgaris*). A portion of, or all of these ingredients may be combined with other ingredients commonly found in anti-aging and repair serum formulations.

*Morinda citrifolia*, as mentioned above, is high in antioxidants that help fight free-radical damage to the skin caused by the sun and other elements. *Morinda citrifolia* is also especially rich in linoleic acid, an essential fatty acid with specific abilities to nourish the skin. This natural ingredient may also be combined with other natural ingredients containing antioxidants, such as *Gingko biloba* extract, grape seed extract, mushroom extract, and vitamins A, C, and E.

Hydrolyzed algin and *chlorella vulgaris* extract (type 1-4) is an extraction essential for protection from UVB rays. This ingredient also stimulates the body's natural production of collagen. Hydrolyzed algin and *chlorella vulgaris* extract (type 1-4) are present in an amount from about 0.001 to 100 percent by weight.

*Rosmarinus officinalis* extract and lecithin serves to stimulate production of lipid-producing cells, which moisturize the skin from the inside out. *Rosmarinus officinalis* extract and lecithin is present in an amount from about 0.001 to 100 percent by weight.

Sodium PCA is a powerful humectant that holds moisture in the skin. Sodium PCA is present in an amount from about 0.001 to 100 percent by weight.

*Hypnea musciformis* extract and mugwort (*artemisia vulgaris*) is designed to calm irritations caused by chemicals and UV rays. *Hypnea musciformis* extract and mugwort (*artemisia vulgaris*) are present in an amount from about 0.001 to 100 percent by weight.

The composition according to the invention also comprises a cosmetically acceptable vehicle to act as a dilutant, dispersant or carrier for the *Morinda citrifolia* or extract in the composition, so as to facilitate its distribution when the composition is applied to the skin.

Vehicles other than or in addition to water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000, mm.sup.3's (centistokes) at 250 degrees Celsius. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5% to 95%, specifically from 25% to 90% by weight of the composition.

The cosmetically acceptable vehicle will usually form from 5% to 99.9%, preferably from 25% to 80% by weight of the composition, and can, in the absence of other cosmetic adjuncts, form the balance of the composition. Specifically, the vehicle is at least 80 wt. % water, by weight of the vehicle. Specifically, water comprises at least 50 wt. % of the inventive composition, specifically from 60 to 80 wt. %, by weight of the composition.

An oil or oily material may be present, together with an emulsifier to provide either a water-in-oil emulsion or an oil-in-water emulsion, depending largely on the average hydrophilic-lipophilic balance (HLB) of the emulsifier employed.

The inventive compositions may also include sun screens. Sun screens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sun screen employed in the emulsions can vary depending upon the degree of protection desired from the sun's UV radiation.

Emollients may further be incorporated into cosmetic compositions of the present invention. Levels of such emollients may range from 0.5% to 50%, preferably between 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as poly-pronylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

The composition according to the invention is intended primarily as a product for topical application to human skin, especially as an agent for conditioning, moisturizing and smoothing the skin, increasing its thickness, flexibility and elasticity and preventing or reducing the appearance of wrinkled, lined or aged skin. The unique formulation of the present invention offers the complete response to the loss of skin tone and promotes immediate and continuous benefits to effectively boost hydration and firmness of the surface layer of the skin, all while working to repair the underlying layers of the skin with antioxidants and other beneficial ingredients to help diminish the appearance of fine lines and wrinkles and to restore visible tone and elasticity to the surface layer of the skin which helps the skin retain its youthful radiance.

In use, a small quantity of the composition, for example from 1 to 100 ml, is applied to exposed areas of the skin, from a suitable container or applicator and, if necessary, it is then spread over and/or rubbed into the skin using the hand or fingers or a suitable device.

The topical skin care composition of the invention can be formulated as a lotion, a cream or a gel. The composition can be packaged in a suitable container to suit its viscosity and intended use by the consumer. For example, a lotion or a cream can be packaged in a bottle or a roll-ball applicator, or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a cosmetically acceptable composition as herein defined.

The following are examples of intensive repair serum formulations comprising *Morinda Citrifolia* therein to create an improved intensive repair serum formulation for various skin types. These examples are merely illustrative and are not meant to be limiting in any way.

EXAMPLE ONE

| Ingredients | Percent by Weight |
| --- | --- |
| Active Ingredients: | |
| Octyl Salicylate | 1–5% |
| Oxybenzone | 1–5% |
| Octyl Methoxy cinnamate | 5–10% |
| Other Ingredients: | |
| *Morinda citrifolia* Fruit Juice | 30–40% |
| Purified Water | 20–30% |
| Glycerin | 10–20% |
| Cyclomethicone | 10–20% |
| *Morinda citrifolia* Seed Oil | 1–5% |
| Distarch Phosphate | 1–5% |
| Pentaerythrityl Tetraisostearate | 1–5% |
| Cetyl Alcohol | 1–5% |
| Glyceryl Stearate | 1–5% |
| PEG-40 Stearate | 0–1% |
| Biosaccharide Gum-1 | 0–1% |
| Cetyl Dimethicone | 0–1% |
| Tocopheryl Acetate (Vitamin E) | 0–1% |
| Sodium Ascorbyl Phosphate | 0–1% |
| Glucosylrutin (Alpha Flavon) | 0–1% |
| Isoquercitin | 0–1% |
| Fragrance | 0–1% |
| Phenoxyethenol | 0–1% |
| Citric Acid | 0–1% |
| EDTA | 0–1% |
| Sodium Hydroxide | 0–1% |
| Methylparaben | 0–1% |
| Ethylparaben | 0–1% |
| Propylparaben | 0–1% |
| Butylparaben | 0–1% |
| Iodopropynyl | 0–1% |
| Butylcarbamate | 0–1% |

EXAMPLE TWO

| Ingredients | Percent by Weight |
| --- | --- |
| Active Ingredients: | |
| Benzophenone-3 | 1–5% |
| Octyl Methoxycinnamate | 5–10% |
| Other Ingredients: | |
| *Morinda citrifolia* Fruit Juice | 30–40% |
| Purified Water | 20–30% |
| Cyclomethicone | 10–20% |
| Hydrogenated Polyisobutene | 10–20% |
| Cetyl Alcohol | 10–20% |
| Glycerin | 10–20% |
| *Morinda citrifolia* Seed Oil | 1–5% |
| Glyceryl Stearate | 1–5% |
| Myristyl Myristate | 1–5% |
| Octyl Palmitate | 1–5% |
| PEG-40 Stearate | 1–5% |
| Vegetable Oil | 1–5% |
| Hydrolyzed Serum Protein | 0–1% |
| Sorbitan Tristearate | 0–1% |
| Retinyl Palmitate | 0–1% |
| Imidazolidinyl Urea | 0–1% |
| Fragrance | 0–1% |
| Polyvinylidene Copolymer | 0–1% |
| propylparaben | 0–1% |
| Tocopheryl Acetate | 0–1% |
| Methylparaben | 0–1% |
| Disodium EDTA | 0–1% |
| Hexamidine | 0–1% |
| Diisethionate | 0–1% |
| Guanosine | 0–1% |
| BHA | 0–1% |
| BHT | 0–1% |

EXAMPLE THREE

| Ingredients | Percent by Weight |
| --- | --- |
| *Morinda citrifolia* Fruit Juice | 30–40% |
| Purified Water | 20–30% |
| Cyclomethicone Dimethicone Crosspolymer | 10–20% |
| *Morinda citrifolia* Seed Oil | 1–5% |
| Acrylates Copolymer | 1–5% |
| Propylene Glycol | 1–5% |
| C12–15 Alkyl Benzoate | 1–5% |
| Retinol | 0–1% |
| Sambucus Nigra Extract | 0–1% |
| Sunflower (Helianthus Annuus) Extract | 0–1% |
| Matricaria (Chamomila Recutita) Extract | 0–1% |
| Primrose (primula Veris) Extract | 0–1% |
| BHT | 0–1% |

EXAMPLE FOUR

| Ingredients | Percent by Weight |
| --- | --- |
| Active Ingredients: | |
| Octyl Methoxycinnamate | 5–10% |
| Other Ingredients: | |
| *Morinda citrifolia* Fruit Juice | 30–40% |
| Purified Water | 20–30% |
| Glycolic Acid | 10–20% |
| Isostearyl Palmitate | 10–20% |
| *Morinda citrifolia* Seed Oil | 1–5% |
| Butylene Glycol | 1–5% |
| C12–15 Alkyl Octanoate | 1–5% |
| Stearic Acid | 1–5% |
| Glycerin | 1–5% |
| PEG-100 Stearate | 1–5% |
| Glyceryl Hydroxystearate | 0–1% |
| Stearyl Alcohol | 0–1% |
| TEA | 0–1% |
| Dimethicone | 0–1% |
| Sorbitan Stearate | 0–1% |
| Hydroxycaprylic Acid | 0–1% |
| Sodium Stearoyl lactylate | 0–1% |
| Retinol | 0–1% |
| Retinyl Palmitate (Vitamin A Palmitate) | 0–1% |
| Retinyl Acetate (Vitamin A Acetate) | 0–1% |
| Tocopheryl Acetate (Vitamin E Acetate) | 0–1% |
| Bisabolol | 0–1% |
| Cholesterol | 0–1% |
| Caprylic/Capric Triglyceride | 0–1% |
| Polysorbate 20 | 0–1% |
| Simethicone | 0–1% |
| Xanthan Gum | 0–1% |
| Magnesium Aluminum Silicate | 0–1% |
| Hydroxyethyl Cellulose | 0–1% |
| Methylparaben | 0–1% |
| Propylparaben | 0–1% |
| Disodium EDTA | 0–1% |
| BHT | 0–1% |
| Ammonium Hydroxide | 0–1% |
| Fragrance | 0–1% |

EXAMPLE FIVE

| Ingredients | Percent by Weight |
| --- | --- |
| *Morinda citrifolia* Fruit Juice | 30–40% |
| Purified Water | 20–30% |
| Witch Hazel Distillate | 10–20% |
| Cucumber Extract | 10–20% |
| *Morinda citrifolia* Seed Oil | 1–5% |

-continued

| Ingredients | Percent by Weight |
|---|---|
| Glycerin | 1–5% |
| Panthenol | 1–5% |
| Hexylene Glycol | 1–5% |
| PEG/PPG-17/6 Copolymer | 1–5% |
| Carbomer | 1–5% |
| Acrylates/C10–C30 Alkyl Acrylate Crosspolymer | 0–1% |
| Sodium Hydroxide | 0–1% |
| Phenoxyethanol | 0–1% |
| Polyglyceryl Methacrylate | 0–1% |
| Imidazolidinyl Urea | 0–1% |
| Methylparaben | 0–1% |
| Sodium Hyaluronate | 0–1% |
| Glycyrrhizic Acid | 0–1% |
| Tetrasodium EDTA | 0–1% |
| Citric Acid | 0–1% |
| Propylene Glycol | 0–1% |
| Chamomile Oil | 0–1% |

EXAMPLE SIX

| Ingredients | Percent by Weight |
|---|---|
| *Morinda citrifolia* Fruit Juice | 30–40% |
| Purified Water | 20–30% |
| Biosaccharide Gum-1 | 5–10% |
| Glycerin | 1–5% |
| Butylene Glycol | 1–5% |
| *Morinda citrifolia* Seed Oil | 1–5% |
| Green Tea (Camellia Sinensis) Leaf Extract | 0–1% |
| Tetrahexyldecyl Ascorbate (Vitamin C) | 0–1% |
| Tocopheryl Acetate (Vitamin E) | 0–1% |
| Grape (Vitis Vinifera) Seed Extract] | 0–1% |
| Lecithin | 0–1% |
| Chlorella Vulgaris Extract | 0–1% |
| Sea Water | 0–1% |
| Algae Extract | 0–1% |
| Hydrolyzed Algin | 0–1% |
| Atlantic Kelp (Laminaria Digitata) Extract] | 0–1% |
| Aloe Vera (Aloe Barbadensis) Leaf Juice | 0–1% |
| Coneflower (Echinacea Purpurea) Extract | 0–1% |
| Gingko Biloba Extract | 0–1% |
| Hydrocotyl (Centella Asiatica) Extract | 0–1% |
| Mugwort (Artemisia Vulgaris) Extract | 0–1% |
| Mushroom (Polyporus Umbellatus) Extract | 0–1% |
| Retinyl Palmitate (Vitamin A) | 0–1% |
| Sodium PCA | 0–1% |
| PEG-40 Hydrogenated Castor Oil | 0–1% |
| Disodium EDTA | 0–1% |
| Carbomer | 0–1% |
| Phenoxyethanol | 0–1% |
| Methylparaben | 0–1% |
| Butylparaben | 0–1% |
| Ethylparaben | 0–1% |
| Propylparaben | 0–1% |
| Xanthan Gum | 0–1% |
| Essential Oils | 0–1% |

The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed is:

1. An intensive repair serum for skin treatment comprising:

*Morinda citrifolia* fruit juice extract present in an amount between about .1 and 80 percent by weight; and an element employed to block ultraviolet light, said element selected from the group consisting of derivatives of PABA, derivatives of cinnamate, octyl methoxy cinnamate, derivatives of salicylate, ocytl salicylate, 2-hydroxy-4-methoxy benzophenone, oxybenzone, benzophenone-3, hydrolyzed algin, and *chlorella vulgaris* extract, present in an amount between 1 and 10 percent by weight.

2. The intensive repair serum of claim 1, wherein said *Morinda citrifolia* fruit juice extract is present in an amount between about 0.1 and 5 percent by weight.

3. The intensive repair serum of claim 1, wherein said *Morinda citrifolia* fruit juice extract is present in an amount between about 5 and 10 percent by weight.

4. The intensive repair serum of claim 1, wherein said *Morinda citrifolia* fruit juice extract is present in an amount between about 10 and 15 percent by weight.

5. The intensive repair serum of claim 1, wherein said *Morinda citrifolia* fruit juice extract is present in an amount between about 15 and 20 percent by weight.

6. The intensive repair serum of claim 1, wherein said *Morinda citrifolia* fruit juice extract is present in an amount between about 20 and 25 percent by weight.

7. The intensive repair serum of claim 1, wherein said *Morinda citrifolia* fruit juice extract is present in an amount between about 25 and 30 percent by weight.

8. The intensive repair serum of claim 1, wherein said *Morinda citrifolia* fruit juice extract is present in an amount between about 30 and 35 percent by weight.

9. The intensive repair serum of claim 1, wherein said *Morinda citrifolia* fruit juice extract is present in an amount between about 35 and 40 percent by weight.

10. The intensive repair serum of claim 1, wherein said *Morinda citrifolia* fruit juice extract is present in an amount between about 40 and 45 percent by weight.

11. The intensive repair serum of claim 1, wherein said *Morinda citrifolia* fruit juice extract is present in an amount between about 45 and 50 percent by weight.

12. The intensive repair serum of claim 1, wherein said *Morinda citrifolia* fruit juice extract is present in an amount between about 0.1 and 40 percent by weight.

13. The intensive repair serum of claim 1, wherein said *Morinda citrifolia* fruit juice extract is present in an amount between about 30 and 40 percent by weight.

14. The intensive repair serum of claim 13, further comprising *Morinda citrifolia* seed oil extract in an amount between about 0.1 and 10 percent by weight.

15. The intensive repair serum of claim 13 further comprising the following ingredients, each in an amount between about 0.001 and 1 percent by weight:

*rosmarinus officinalis* extract;

lecithin;

Sodium PCA;

*hypnea musciformis* extract; and and mugwort.

16. The intensive repair serum of claim 13 further comprising:

a silicone carrier in an amount between about 20 and 80 percent by weight;

an antioxidant in an amount between about 0.001 and 1 percent by weight;

water in an amount between about 60 and 80 percent by weight;

a sun screen agent in amount between about 0.001 and 1 percent by weight;

an emollient in an amount between about 5 and 30 percent by weight;

an emulsifier in an amount between about 0.001 and 30 percent by weight;

a humectant in an amount between about 0.001 and 30 percent by weight; and a thickener in an amount between about 0.1 to 0.2 percent by weight.

17. The intensive repair serum of claim 1, wherein said *Morinda citrifolia* fruit juice extract is processed.

18. The intensive repair serum of claim 1, further comprising water present in an amount between about 20 and 80 percent by weight.

19. The intensive repair serum of claim 1, wherein said octyl salicylate is present in an amount between about 1 and 5 percent by weight.

20. The intensive repair serum of claim 1, wherein said oxybenzone is present in an amount between about 1 and 5 percent by weight.

21. The intensive repair serum of claim 1, wherein said octyl methoxycinnamate is present in an amount between about 5 and 10 percent by weight.

22. The intensive repair serum of claim 1, further comprising glycerin present in an amount between about 1 and 20 percent by weight.

23. The intensive repair serum of claim 1, further comprising cyclomethicone present in an amount between about 10 and 20 percent by weight.

24. The intensive repair serum of claim 1, further comprising *Morinda citrifolia* seed oil present in an amount between about 1 and 5 percent by weight.

25. The intensive repair serum of claim 1, further comprising distarch phosphate present in an amount between about 1 and 5 percent by weight.

26. The intensive repair serum of claim 1, further comprising pentaerythrityl tetraisostearate present in an amount between about 1 and 5 percent by weight.

27. The intensive repair serum of claim 1, further comprising cetyl alcohol present in an amount between about 1 and 5 percent by weight.

28. The intensive repair serum of claim 1, further comprising glyceryl stearate present in an amount between about 1 and 5 percent by weight.

29. The intensive repair serum of claim 1, further comprising hydrogenated polyisobutene present in an amount between about 10 and 20 percent by weight.

30. The intensive repair serum of claim 1, further comprising cetyl alcohol present in an amount between about 10 and 20 percent by weight.

31. The intensive repair serum of claim 1, further comprising myristyl myristate present in an amount between about 1 and 5 percent by weight.

32. The intensive repair serum of claim 1, further comprising octyl palmitate present in an amount between about 1 and 5 percent by weight.

33. The intensive repair serum of claim 1, further comprising PEG-40 stearate present in an amount between about 1 and 5 percent by weight.

34. The intensive repair serum of claim 1, further comprising vegetable oil present in an amount between about 1 and 5 percent by weight.

35. The intensive repair serum of claim 1, further comprising cyclomethicone dimethicone crosspolymer present in an amount between about 10 and 20 percent by weight.

36. The intensive repair serum of claim 1, further comprising acrylates copolymer present in an amount between about 1 and 5 percent by weight.

37. The intensive repair serum of claim 1, further comprising propylene glycol present in an amount between about 1 and 5 percent by weight.

38. The intensive repair serum of claim 1, further comprising C12–15 alkyl benzoate present in an amount between about 1 and 5 percent by weight.

39. The intensive repair serum of claim 1, further comprising glycolic acid present in an amount between about 10 and 20 percent by weight.

40. The intensive repair serum of claim 1, further comprising isostearyl palmitate present in an amount between about 10 and 20 percent by weight.

41. The intensive repair serum of claim 1, further comprising butylene glycol present in an amount between about 1 and 5 percent by weight.

42. The intensive repair serum of claim 1, further comprising C12–15 alkyl octanoate present in an amount between about 1 and 5 percent by weight.

43. The intensive repair serum of claim 1, further comprising stearic acid present in an amount between about 1 and 5 percent by weight.

44. The intensive repair serum of claim 1, further comprising PEG-100 stearate present in an amount between about 1 and 5 percent by weight.

45. The intensive repair serum of claim 1, further comprising witch hazel distillate present in an amount between about 10 and 20 percent by weight.

46. The intensive repair serum of claim 1, further comprising cucumber extract present in an amount between about 10 and 20 percent by weight.

47. The intensive repair serum of claim 1, further comprising panthenol present in an amount between about 1 and 5 percent by weight.

48. The intensive repair serum of claim 1, further comprising hexylene glycol present in an amount between about 1 and 5 percent by weight.

49. The intensive repair serum of claim 1, further comprising PEG/PPG-17/6 copolymer present in an amount between about 1 and 5 percent by weight.

50. The intensive repair serum of claim 1, further comprising carbomer present in an amount between about 5 and 5 percent by weight.

51. The intensive repair serum of claim 1, further comprising biosaccharide gum-1 present in an amount between about 5 and 10 percent by weight.

52. The intensive repair serum of claim 1, further comprising ingredients selected from the group consisting of PEG-40 Stearate, Biosaccharide Gum-1, Cetyl Dimethicone, Tocopheryl Acetate (Vitamin E), Sodium Ascorbyl Phosphate, Glucosylrutin (Alpha Flavon), Isoquercitin, Fragrance, Phenoxyethenol, Citric Acid, EDTA, Sodium Hydroxide, Methylparaben, Ethylparaben, Propylparaben, Butylparaben, Iodopropynyl, and Butylcarbamate, each present in an amount between about 0 and 1 percent by weight.

53. The intensive repair serum of claim 1, further comprising ingredients selected from the group consisting of Hydrolyzed Serum Protein, Sorbitan Tristearate, Retinyl Palmitate, Imidazolidinyl Urea, Fragrance, Polyvinylidene Copolymer, propylparaben, Tocopheryl Acetate, Methylparaben, Disodium EDTA, Hexamidine, Diisethionate, Guanosine, BHA, and BHT, each present in an amount between about 0 and 1 percent by weight.

54. The intensive repair serum of claim 1, further comprising ingredients selected from the group consisting of Retinol, *Sambucus Nigra* Extract, Sunflower (*Helianthus Annuus*) Extract, Matricaria (*Chamomila Recutita*) Extract, Primrose (*primula Veris*) Extract, and BHT, each present in an amount between about 0 and 1 percent by weight.

55. The intensive repair serum of claim 1, further comprising ingredients selected from the group consisting of Glyceryl Hydroxystearate, Stearyl Alcohol, TEA, Dimethicone, Sorbitan Stearate, Hydroxycaprylic Acid, Sodium Stearoyl lactylate, Retinol, Retinyl Palmitate (Vitamin A Palmitate), Retinyl Acetate (Vitamin A Acetate), Tocopheryl Acetate (Vitamin E Acetate), Bisabolol, Cholesterol, Caprylic/Capric Triglyceride, Polysorbate 20, Simethicone, Xanthan Gum, Magnesium Aluminum Silicate, Hydroxyethyl Cellulose, Methylparaben, Propylparaben, Disodium EDTA, BHT, Ammonium Hydroxide, and Fragrance, each present in an amount between about 0 and 1 percent by weight.

56. The intensive repair serum of claim 1, further comprising ingredients selected from the group consisting of Acrylates/C10–C30 Alkyl Acrylate Crosspolymer, Sodium Hydroxide, Phenoxyethanol, Polyglyceryl Methacrylate, Imidazolidinyl Urea, Methylparaben, Sodium Hyaluronate, Glycyrrhizic Acid, Tetrasodium EDTA, Citric Acid, Propylene Glycol, and Chamomile Oil, each present in an amount between about 0 and 1 percent by weight.

57. The intensive repair serum of claim 1, further comprising ingredients selected from the group consisting of Green Tea (*Camellia Sinensis*) Leaf Extract, Tetrahexyldecyl Ascorbate (Vitamin C), Tocopheryl Acetate (Vitamin E), Grape (*Vitis Vinifera*) Seed Extract, Lecithin, *Chlorella Vulgaris* Extract, Sea Water, Algae Extract, Hydrolyzed Algin, Atlantic Kelp (*Laminaria Digitata*) Extract, Aloe Vera (*Aloe Barbadensis*) Leaf Juice, Coneflower (*Echinacea Purpurea*) Extract, Gingko Biloba Extract, Hydrocotyl (*Centella Asiatica*) Extract, Mugwort (*Artemisia Vulgaris*) Extract, Mushroom (*Polyporus Umbellatus*) Extract, Retinyl Palmitate (Vitamin A), Sodium PCA, PEG40 Hydrogenated Castor Oil, Disodium EDTA, Carbomer, Phenoxyethanol, Methylparaben, Butylparaben, Ethylparaben, Propylparaben, Xanthan Gum, and Essential Oils, each present in an amount between about 0 and 1 percent by weight.

58. An intensive repair serum for skin treatment comprising:
*Morinda citrifolia* fruit juice extract present in an amount between about 0.1 and 80 percent by weight;
*Morinda citrifolia* seed oil present in an amount between about 1 and 5 percent by weight;
PEG-40 hydrogenated castor oil; and
an ingredient selected from the group consisting of hydrolyzed algin, *chlorella vulgaris* extract, *rosmarinus officinalis* leaf extract, *artemisia vulgaris* extract, *vitis vinifera* extract, *polyporus umbellatus* extract, *camellia sinensis* leaf extract, *laminaria digitata* extract, *aloe barbadensis* leaf juice, *echinacea purpurea* extract, *gingko biloba* extract, *centella asiatica* extract, and algae extract.

59. An intensive repair serum for skin treatment comprising:
*Morinda citrifolia* fruit juice extract present in an amount between about 0.1 and 80 percent by weight;
*Morinda citrifolia* seed oil present in an amount between about 1 and 5 percent by weight; and
ingredients selected from the group consisting of retinol, retinyl palmitate, retyinyl acetate, tocopheryl acetate, tetrahexyldecyl ascorbate, *chamomila recutita* extract, chamomile oil, essential oils, *helianthus annuus* extract, *hypnea musciformis* extract, lecithin, *primula veris* extract, *sambucus sigra* extract, sea water, hydrolyzed algin, *chlorella vulgaris* extract, *rosmarinus officinalis* leaf extract, *artemisia vulgaris* extract, *vitis vinifera* extract, *polyporus umbellatus* extract, *camellia sinensis* leaf extract, *laminaria digitata* extract, *aloe barbadensis* leaf juice, *echinacea purpurea* extract, *gingko biloba* extract, *centella asiatica* extract, and algae extract.

* * * * *